United States Patent [19]

Heasley

[11] 4,338,311

[45] Jul. 6, 1982

[54] HYDROPHILIC CHOLINE SALICYLATE FORMULATION

[75] Inventor: Ralph A. Heasley, Woodbury, Minn.

[73] Assignee: Riker Laboratories, Inc., Northridge, Calif.

[21] Appl. No.: 201,175

[22] Filed: Oct. 27, 1980

[51] Int. Cl.³ .......................................... A61K 31/615
[52] U.S. Cl. ....................................................... 424/233
[58] Field of Search ................................. 424/230–235

[56] References Cited

U.S. PATENT DOCUMENTS

| | | | |
|---|---|---|---|
| 3,297,529 | 1/1967 | Berke | 424/230 |
| 3,759,980 | 9/1973 | Rosen et al. | 260/480 |
| 3,801,613 | 4/1974 | Swimm | 260/448.2 N |
| 3,898,332 | 8/1975 | Swimm | 424/184 |
| 3,947,491 | 3/1976 | Kelly et al. | 260/501.15 |
| 3,965,263 | 6/1976 | Swimm | 424/184 |
| 4,067,974 | 1/1978 | Sasmar | 424/231 |
| 4,098,818 | 7/1978 | Krummel et al. | 260/535 R |
| 4,147,776 | 4/1979 | Kelly et al. | 424/175 |

Primary Examiner—Stanley J. Friedman
Attorney, Agent, or Firm—Cruzan Alexnader; Donald M. Sell; Donald C. Gipple

[57] ABSTRACT

Stable, solid formulations of choline salicylate and hydrophilic silicon dioxide, a process for their preparation and a method for their use.

5 Claims, No Drawings

HYDROPHILIC CHOLINE SALICYLATE FORMULATION

This invention relates to stable, solid choline salicylate formulations with hydrophilic silicon dioxide, to a process for their preparation and to a method for the use thereof.

The formulations are particularly useful for inducing analgesia, reducing fever and reducing inflammation. They are stable under normal storage conditions yet readily dissolve in water. This desirable combination of properties is, furthermore, obtained without the inclusion of metal ions.

Choline salicylate is well known to provide good salicylate levels in the blood, thereby inducing analgesia, reducing fever and reducing inflammation and can be prepared by suspending a choline salt in a suitable inert solvent, adding a metal salicylate salt and removing the solvent. See, for example, U.S. Pat. Nos. 3,069,321 and 3,801,613. It is a very hydroscopic substance (i.e., it readily absorbs and adsorbs water) and is highly water soluble. For some purposes this hygroscopicity is advantageous. However, when preparing tablets, granules and capsules and other solid dosage forms of choline salicylate it is a severe disadvantage due to the resulting instability of the product under normal storage conditions.

A variety of approaches have been used to overcome this difficulty. Thus, mixtures of choline salicylate and magnesium sulfate, of magnesium cation, choline cation and an anion selected from salicylate and acetylsalicylate and of choline salicylate mixed with a metal salicylate having a valence of at least two (preferably with carboxymethyl cellulose added) have been utilized (U.S. Pat. Nos. 3,297,529, 3,759,980 and 4,067,974, respectively) as have complexes of choline salicylate with alkali metal sulfites (U.S. Pat. No. 3,947,491) and choline salicylate compositions containing sulfite, bisulfite, metabisulfite, dithionate, hydrosulfite or hyposulfite metal salts (U.S. Pat. Nos. 4,098,813 and 4,147,776). However, none of them describe formulations at all similar to those of the present invention or provide a completely acceptable choline salicylate formulation.

U.S. Pat. Nos. 3,801,613, 3,898,332 and 3,965,263 describe formulations of choline salicylate and silanized silicon dioxide. Silanized silicon dioxide is, however, hydrophobic and the formulations thereof with choline salicylate are very different from those of the formulations of the present invention. Specifically, they dissolve in water at an undesirably low rate.

The formulations of the present invention comprise intimate mixtures of from about 25 to 60 parts by weight of hydrophilic silicon dioxide (e.g., pyrogenic silica or silica gel) and 75 to 40 parts by weight of choline salicylate (the sum of the two always being 100 parts by weight herein). The formulations of the invention which are capable of being pressed into tablets contain at least about 35 parts of silica. Preferably the formulations contain from about 35 to 45 parts by weight of the (biologically inert) hydrophilic silicon dioxide carrier due to the resulting combination of desirable physical properties (relative non-deliquescence, relatively rapid dissolution in water, capability of tabletting and flowability as a powder and high concentration of active ingredient (choline salicylate). Formulations containing less than about 25 parts carrier are undesirably hygroscopic and deliquescent and are not included within the invention.

Choline salicylate is conveniently prepared by mixing a choline salt (such as a halide, preferably choline chloride) and a metal salicylate salt (e.g., an alkali metal, preferably sodium, salt) in an inert solvent (suspending the choline salt in the solvent then adding the salicylate salt) then cooling and filtering to remove the insoluble inorganic salt. The hydrophilic silicon dioxide can then be added to the choline salicylate solution, the resulting slurry mixed and the solvent removed by evaporation and drying. Thus, the preparative process comprises the following steps:

(1) suspending a choline salt in an inert solvent,
(2) adding a metal salicylate salt,
(3) mixing,
(4) cooling the reaction mixture and filtering to remove the inorganic salt,
(5) adding an amount of hydrophilic silica sufficient to provide a mixture of 25 to 60 parts by weight of the hydrophilic silicon dioxide and 75 to 40 parts by weight of choline salicylate,
(6) evaporating the residual solvent, and
(7) drying the recovered choline salicylate hydrophilic silica formulation.

The resulting powder of choline salicylate and silicon dioxide is further formulated if desired into tablets, granules, capsules and other suitable dosage forms. The solvents used in the preparation of the choline salicylate solutions are preferably free of water, although small amounts (less than 5 percent) of water are not a serious deficiency. Suitable solvents for both steps include acetone and other low molecular weight ketones, isopropyl alcohol and other low molecular weight alcohols, ethyl acetate and the like.

Suitable forms of hydrophilic silicon dioxide for use in the practice of the invention include, but are not limited to, pyrogenic silicon dioxide (available for example under the trade designation Cab-O-Sil from the Cabot Corporation of Tuscola, Ill.) and hyrolyzed silica gel (available under the trade designation Syloid from Davison Chemical of Baltimore, Md.).

The formulations of the invention possess excellent water solubility when compared to the water solubility of formulations of choline salicylate and silanized silicon dioxide described in the prior art and when administered to mammals provide blood levels of salicylate sufficient to result in relatively high pharmacological activity as analgesics, antipyretics and antiinflammatory agents. Thus, when a 60/40 formulation of choline salicylate-pyrogenic silicon dioxide is dissoved in water at 37° C. in a United States Pharmacopoeial dissolution apparatus; it is over 70 percent dissolved in 2 minutes and over 98 percent dissolved in 10 minutes.

The following examples are illustrative of the present invention but are in no way limiting thereof. The parts and percentages referred to in the examples and throughout the specification and claims are by weight and are based on 100 parts or 100 percent of choline salicylate plus hydrophilic silicon dioxide (silica) unless otherwise stated. Also, the parts and the percentages and other amounts refer to anhydrous materials, also unless otherwise specified.

EXAMPLE 1

A mixture of 6.95 g of choline chloride, 8.0 g sodium salicylate and 100 ml of acetone is warmed slightly, then stirred for about 30 minutes. The mixture is cooled and filtered to remove the solid sodium chloride precipitate. The solvent is removed by evaporation leaving a residue of choline salicylate which crystallizes under dry conditions.

EXAMPLE 2

The formulations of choline salicylate and pyrogenic silicon dioxide shown in Table I are prepared by mixing the ingredients in acetone, evaporating the acetone and drying the samples overnight in a drying oven heated at 30° C.

TABLE I

| Sample No. | Weight of Choline Salicylate (in g) | Weight of Pyrogenic Silica gel (in g) | % Choline Salicylate | % Pyrogenic Silica |
|---|---|---|---|---|
| 1 | 0.5 | 0.0 | 100 | 0 |
| 2 | 0.5 | 0.125 | 80 | 20 |
| 3 | 0.5 | 0.214 | 70 | 30 |
| 4 | 0.5 | 0.333 | 60 | 40 |
| 5 | 0.5 | 0.50 | 50 | 50 |
| 6 | 0.5 | 0.75 | 40 | 60 |
| 7 | 0.5 | 1.00 | 33 | 67 |
| 8 | 0.0 | 0.5 | 0 | 100 |

These samples are weighed, subjected to a test period of 30 days at room temperature (approximately 20°–22° C.) and 79% relative humidity then weighed again. The weight gains noted (due to absorption of atmospheric moisture) are as follows:

TABLE II

| Sample No. | Weight Gain % at 79% Relative Humidity for 30 Days |
|---|---|
| 1 | 35.4 |
| 2 | 37.0 |
| 3 | 38.0 |
| 4 | 29.3 |
| 5 | 23.1 |
| 6 | 18.0 |
| 7 | 14.1 |
| 8 | 1.8 |

The formulations of samples 4–7 remain as solid, flowable powders at the end of the test period (30 days at 79 percent relative humidity). Although sample 3 is not a flowable powder after this relatively extreme storage test, it is non-deliquescent, remains as a flowable powder after more moderate storage conditions and it is capable of being tabletted. Also, it dissolves rapidly in water and, of course, it contains a quite high concentration of the active ingredient, choline salicylate.

EXAMPLE 3

A solution of 11.004 g of choline salicylate in 50 ml of acetone is added to a mixture of 7.33 g of pyrogenic silicon dioxide and 60 ml of acetone. All of the solvent is removed by evaporation, and the solid is dried in a vacuum oven at 30° C. in the presence of phosphorus pentoxide. The product is 17.5 g (a 95% yield) of choline salicylate-silicon dioxide (60/40 ratio).

The dissolution rate of this formulation is measured in 900 ml of distilled water at 50 rpm using the U.S.P. II dissolution apparatus. Spectrophotometric analysis of the samples is carried out on a Cary 15 ultraviolet spectrophotometer at 295.5 m$\mu$ using 0.100 cm cells. A sample of the solution is withdrawn at each time point, filtered through a 3 micron filter, stored in glass screw cap vials and analyzed. Two trials are made and the results are shown in Tables III and IV.

TABLE III

| TRIAL 1 (0.7307 g formulation, 0.438 g choline salicylate) | | | | | | | |
|---|---|---|---|---|---|---|---|
| Time (minutes) | 0 | 2 | 5 | 10 | 20 | 40 | ∞ |
| Absorbance (at 295.5 m$\mu$) | 0 | 0.635 | 0.695 | 0.711 | 0.715 | 0.716 | 0.711 |
| Concentration (mg/ml) | 0 | 0.432 | 0.473 | 0.484 | 0.486 | 0.487 | 0.484 |
| Percent Dissolved | 0 | 88.8 | 97.1 | 99.4 | 99.9 | 100 | 99.4 |

TABLE IV

| TRIAL 2 (0.7240 g formulation, 0.434 g choline salicylate) | | | | | | | |
|---|---|---|---|---|---|---|---|
| Time (minutes) | 0 | 2 | 5 | 10 | 20 | 40 | ∞ |
| Absorbance (at 295.5 m$\mu$) | 0 | 0.521 | 0.551 | 0.702 | 0.712 | 0.714 | 0.720 |
| Concentration (mg/ml) | 0 | 0.354 | 0.375 | 0.478 | 0.484 | 0.486 | 0.490 |
| Percent Dissolved | 0 | 72.8 | 77.0 | 98.1 | 99.5 | 99.8 | 100 |
| Average Percent Dissolved | 0 | 80.8 | 87.0 | 98.8 | 99.7 | 99.9 | 100 |

EXAMPLE 4

A solution of 15 ml of acetone containing 0.5257 g of choline salicylate is added to 0.3505 g of hydrolyzed silica gel and the mixture is evaporated under vacuum to provide a 60/40 choline salicylate-silicone dioxide formulation. The formulation is a white to off-white, free-flowing powder.

EXAMPLE 5

A sample of a 60 percent pyrogenic silicon dioxide/40 percent choline salicylate formulation is compressed on a laboratory tablet maker to provide a tablet. The tablet is 11/32 inches in diameter, weighs 0.245 g and is 0.504 cm thick.

EXAMPLE 6

A sample of 60 percent choline salicylate and 40 percent hydrophilic silicone dioxide is formulated into 00 capsules. Using the standard USP disintegration apparatus and a medium of 0.1 N hydrocholoric acid at 37° C., a disintegration time of 4.00 minutes is recorded.

What is claimed is:

1. A method for the preparation of a formulation comprising 25 to 60 parts by weight of hydrophilic silicon dioxide and 75 to 40 parts by weight of choline salicylate, the sum of the parts of hydrophilic silicon dioxide and choline salicylate being 100, which comprises the steps of:
   (1) suspending a choline salt in an inert solvent,
   (2) adding a metal salicylate salt,
   (3) mixing,
   (4) cooling the reaction mixture and filtering to remove the inorganic salt,
   (5) adding an amount of hydrophilic silica to provide a proportion of hydrophilic silicon dioxide to choline salicylate within the specified range,
   (6) evaporating the residual solvent, and
   (7) drying the recovered choline salicylate hydrophilic silica formulation.

2. A hydrophilic choline salicylate formulation prepared by the process of claim 1 comprising 25 to 60 parts by weight of hydrophilic silicon dioxide and 75 to 40 parts by weight of choline salicylate, the sum of the parts of hydrophilic silicon dioxide and choline salicylate being 100.

3. A formulation according to claim 1 which contains at least 35 parts by weight of hydrophilic silicon dioxide.

4. A formulation according to claim 1 which contains from about 35 to 45 parts by weight of hydrophilic silicon dioxide.

5. A method for providing biologically active blood levels of salicylate to a mammal from a solid formulation comprising administering orally a formulation according to claim 1 in suitable dose size and form.

* * * * *